(12) United States Patent
Gliner et al.

(10) Patent No.: US 11,317,966 B2
(45) Date of Patent: May 3, 2022

(54) IMPEDANCE-BASED POSITION TRACKING PERFORMANCE USING SCATTERED INTERPOLANT

(71) Applicant: BIOSENSE WEBSTER (ISRAEL) LTD., Yokneam (IL)

(72) Inventors: Vadim Gliner, Haifa (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 316 days.

(21) Appl. No.: 15/653,643

(22) Filed: Jul. 19, 2017

(65) Prior Publication Data

US 2019/0021789 A1 Jan. 24, 2019

(51) Int. Cl.
*A61B 18/14* (2006.01)
*A61B 5/06* (2006.01)
(Continued)

(52) U.S. Cl.
CPC .......... *A61B 18/1492* (2013.01); *A61B 5/029* (2013.01); *A61B 5/0215* (2013.01);
(Continued)

(58) Field of Classification Search
CPC ..... A61B 18/1492; A61B 18/20; A61B 18/02; A61B 18/14; A61B 18/18; A61B 18/24;
(Continued)

(56) References Cited

U.S. PATENT DOCUMENTS

| 5,391,199 A | 2/1995 | Ben-Haim |
| 5,956,418 A | 9/1999 | Mger et al. |

(Continued)

FOREIGN PATENT DOCUMENTS

| JP | 2014-530030 A | 11/2014 |
| JP | 2017-047214 A | 3/2017 |

(Continued)

OTHER PUBLICATIONS

Steoimen Popv, Binary Search, https://github.com/stoimen/algorithms/wiki/Binary-Search, Oct. 16, 2015, retrieved Aug. 27, 2019 (Year: 2015).*

(Continued)

*Primary Examiner* — Amelie R Davis
*Assistant Examiner* — John Denny Li
(74) *Attorney, Agent, or Firm* — Dergosits & Noah LLP; Todd A. Noah

(57) ABSTRACT

A method includes, receiving from a calibration probe multiple data points acquired in an organ of a patient, each data point including (i) a respective position of the calibration probe, and (ii) a respective set of electrical values indicative of respective impedances between the position and multiple electrodes attached externally to the patient. A mapping between sets of the electrical values and respective positions in the organ is constructed, by performing for each received data point: if the mapping already contains one or more existing data points in a predefined vicinity of the data point, the one or more existing data points are adjusted responsively to the received data point, and if the predefined vicinity does not contain any existing data points, the received data point is added to the mapping. A position of a medical probe is subsequently tracked in the organ using the mapping.

16 Claims, 3 Drawing Sheets

(51) Int. Cl.

| | |
|---|---|
| *A61B 5/0538* | (2021.01) |
| *A61B 5/0536* | (2021.01) |
| *A61B 5/285* | (2021.01) |
| *A61B 5/287* | (2021.01) |
| *A61B 34/20* | (2016.01) |
| *A61B 18/20* | (2006.01) |
| *A61M 25/01* | (2006.01) |
| *A61B 5/053* | (2021.01) |
| *A61B 5/00* | (2006.01) |
| *A61B 5/0215* | (2006.01) |
| *A61B 5/029* | (2006.01) |
| *A61B 5/145* | (2006.01) |
| *A61B 8/08* | (2006.01) |
| *A61N 1/06* | (2006.01) |
| *A61N 1/32* | (2006.01) |
| *A61N 1/365* | (2006.01) |
| *A61N 1/40* | (2006.01) |
| *A61N 1/00* | (2006.01) |
| *A61B 18/00* | (2006.01) |
| *A61B 18/16* | (2006.01) |
| *A61B 18/12* | (2006.01) |
| *A61B 5/352* | (2021.01) |
| *A61B 90/00* | (2016.01) |
| *A61B 1/273* | (2006.01) |
| *A61B 18/02* | (2006.01) |
| *A61B 18/18* | (2006.01) |
| *A61B 18/24* | (2006.01) |
| *A61B 17/00* | (2006.01) |
| *A61N 1/362* | (2006.01) |

(52) U.S. Cl.
CPC .......... *A61B 5/0536* (2013.01); *A61B 5/0538* (2013.01); *A61B 5/06* (2013.01); *A61B 5/062* (2013.01); *A61B 5/063* (2013.01); *A61B 5/065* (2013.01); *A61B 5/145* (2013.01); *A61B 5/285* (2021.01); *A61B 5/287* (2021.01); *A61B 8/0833* (2013.01); *A61B 18/20* (2013.01); *A61B 34/20* (2016.02); *A61M 25/0147* (2013.01); *A61N 1/06* (2013.01); *A61N 1/32* (2013.01); *A61N 1/36564* (2013.01); *A61N 1/403* (2013.01); *A61B 1/2733* (2013.01); *A61B 5/0044* (2013.01); *A61B 5/053* (2013.01); *A61B 5/352* (2021.01); *A61B 5/6852* (2013.01); *A61B 18/02* (2013.01); *A61B 18/14* (2013.01); *A61B 18/18* (2013.01); *A61B 18/24* (2013.01); *A61B 2017/00243* (2013.01); *A61B 2017/00247* (2013.01); *A61B 2018/00392* (2013.01); *A61B 2018/00702* (2013.01); *A61B 2018/00839* (2013.01); *A61B 2018/00875* (2013.01); *A61B 2018/1253* (2013.01); *A61B 2018/162* (2013.01); *A61B 2034/2046* (2016.02); *A61B 2034/2051* (2016.02); *A61B 2034/2053* (2016.02); *A61B 2090/367* (2016.02); *A61B 2090/3958* (2016.02); *A61B 2560/0238* (2013.01); *A61M 25/0127* (2013.01); *A61N 1/00* (2013.01); *A61N 1/3621* (2013.01); *A61N 1/3627* (2013.01)

(58) Field of Classification Search
CPC ....... A61B 34/20; A61B 5/0215; A61B 5/029; A61B 5/0421; A61B 5/0422; A61B 5/06; A61B 5/065; A61B 5/145; A61B 5/0456; A61B 8/0833; A61B 2034/2051; A61B 2090/367; A61B 2090/3958; A61B 1/2733; A61B 2017/00243; A61B 2017/00247; A61B 2018/00392; A61M 25/0147; A61M 25/0127; A61N 1/06; A61N 1/32; A61N 1/36564; A61N 1/403; A61N 1/3621; A61N 1/3627
See application file for complete search history.

(56) References Cited

U.S. PATENT DOCUMENTS

| | | | |
|---|---|---|---|
| 6,239,724 | B1 | 5/2001 | Doron et al. |
| 6,332,089 | B1 | 12/2001 | Acker et al. |
| 6,484,118 | B1 | 11/2002 | Govari |
| 6,618,612 | B1 | 9/2003 | Acker et al. |
| 6,690,963 | B2 | 2/2004 | Ben-Haim et al. |
| 8,456,182 | B2 | 6/2013 | Bar-Tal et al. |
| 2002/0033454 | A1 | 3/2002 | Cheng et al. |
| 2002/0065455 | A1 | 5/2002 | Ben-Haim et al. |
| 2003/0120150 | A1 | 6/2003 | Govari |
| 2004/0068178 | A1 | 4/2004 | Govari |
| 2006/0178828 | A1 | 8/2006 | Moravec |
| 2008/0009711 | A1* | 1/2008 | Govari ............... A61B 5/06 600/424 |
| 2009/0099468 | A1* | 4/2009 | Thiagalingam ...... A61B 5/0452 600/515 |
| 2009/0264760 | A1 | 10/2009 | Lazebnik et al. |
| 2012/0194516 | A1 | 8/2012 | Newcombe et al. |
| 2013/0066193 | A1* | 3/2013 | Olson ................ A61B 5/062 600/424 |
| 2013/0202177 | A1 | 8/2013 | Bar-Aviv et al. |
| 2014/0232717 | A1 | 8/2014 | Schpok |
| 2015/0141798 | A1 | 5/2015 | Bar-Tal |
| 2016/0196666 | A1 | 7/2016 | Venkatraghavan |
| 2017/0065353 | A1 | 3/2017 | Ludwin et al. |
| 2017/0325891 | A1* | 11/2017 | Harlev ................ A61B 34/10 |

FOREIGN PATENT DOCUMENTS

| | | | | |
|---|---|---|---|---|
| WO | WO 96/05768 | A1 | 2/1996 | |
| WO | WO-2009129475 | A1 * | 10/2009 | ............ A61B 5/053 |
| WO | 2013039564 | A3 | 3/2013 | |

OTHER PUBLICATIONS

Yang et al., A Study of the 12 Different Interpolation Methods—A Case Study of SURFER 8.0, Proceedings of the XXth ISPRS Congress, 2004 (Year: 2004).*

European Search Report dated Nov. 11, 2018 from corresponding European Patent Application No. 18184126.3.

Inverse Distance Weighting: Difference Between Revisions—Wikipedia, Dec. 10, 2015, URL: https://en.wikipedia.org/w/index.php?title=inverse_distance_weighing&dif=695845427&oldid=65058.

Search Report from corresponding Japanese Patent Application No. 2018-134773, dated Feb. 28, 2022.

Notice of Reasons for Refusal from corresponding Japanese Patent Application No. 2018-134773, dated Mar. 15, 2022.

* cited by examiner

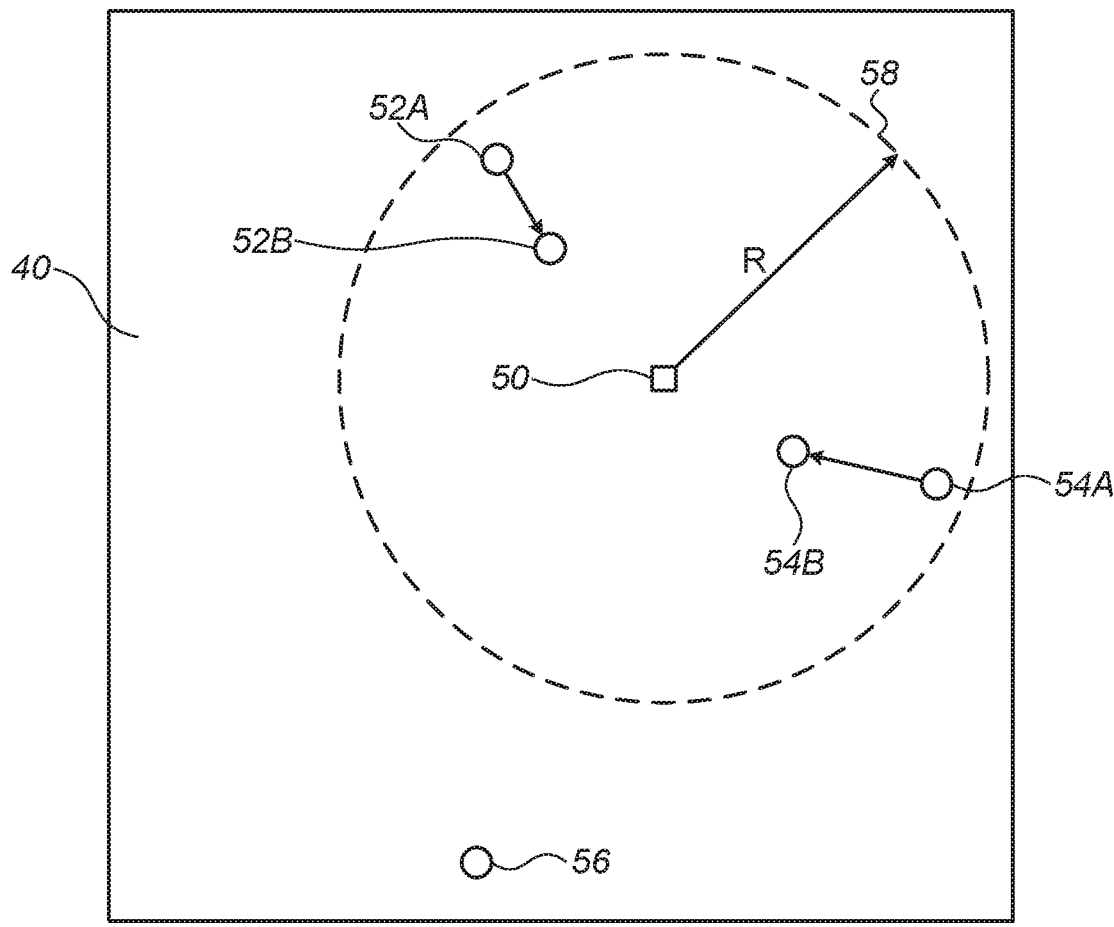
FIG. 2
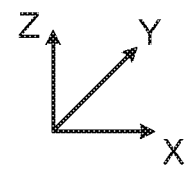

IMPEDANCE-BASED POSITION TRACKING PERFORMANCE USING SCATTERED INTERPOLANT

FIELD OF THE INVENTION

The present invention relates generally to position tracking of medical probes, and particularly to methods and systems for impedance-based position tracking of a medical tool.

BACKGROUND OF THE INVENTION

Various tracking techniques, such as active current location (ACL) and magnetic position sensing, may be used for tracking the position of a medical probe, e.g., a catheter, in a patient body.

For example, U.S. Patent Application Publication 2014/0232717 describes systems and methods for merging three-dimensional models, such as a three-dimensional range sensor-based model and a three-dimensional camera-based model, are provided. According to aspects of the present disclosure, an enhanced volumetric merging technique can be used to merge the three-dimensional models.

U.S. Patent Application Publication 2006/0178828 describes a method for generating an evidence grid representing an environment. The method comprises the steps of collecting a set of stereo images at multiple locations within the environment using stereo sensors, and processing the set of stereo images to determine occupancy and distance data associated with each point in space represented in the set of stereo images; applying a sensor model to each point in space to determine a probability of occupancy of each voxel representing each point in space; and generating an evidence grid of the environment by combining the probabilities for each voxel.

SUMMARY OF THE INVENTION

An embodiment of the present invention that is described herein provides a method, including receiving from a calibration probe multiple data points acquired in an organ of a patient, each data point including (i) a respective position of the calibration probe, and (ii) a respective set of electrical values indicative of respective impedances between the position and multiple electrodes attached externally to the patient. A mapping between sets of the electrical values and respective positions in the organ is constructed, by performing for each received data point: if the mapping already contains one or more existing data points in a predefined vicinity of the data point, the one or more existing data points are adjusted responsively to the received data point, and if the predefined vicinity does not contain any existing data points, the received data point is added to the mapping. A position of a medical probe is subsequently tracked in the organ using the mapping.

In some embodiments, constructing the mapping includes finding the one or more existing data points that fall in the predefined vicinity, by sorting at least some of the data points in the mapping according to their respective distances from the received data point. In other embodiments, sorting the data points includes applying a binary searching technique. In yet other embodiments, the calibration probe includes a magnetic position sensor of a magnetic position tracking system.

In an embodiment, the predefined vicinity includes a circle defined by a radius smaller than 10 mm, centered at the position specified in the received data point. In another embodiment, adjusting the one or more existing data points includes calculating a weighted arithmetic average of the position and the electrical values between the one or more existing data points and the received data point, and adjusting the position and the electrical values of the one or more existing data points by applying a scattered interpolant process.

In some embodiments, tracking the position includes: receiving from the medical probe, at a given location in the organ, a given set of the electrical values, selecting from among the data points of the mapping data points including electrical values falling within a predefined range of electrical values including the given set, and estimating the position of the medical probe at the given location by identifying one or more of the selected data points having electrical values closest to the electrical values of the given set. In other embodiments, identifying the one or more of the selected data points includes applying a binary searching technique.

There is additionally provided, in accordance with an embodiment of the present invention, an apparatus that includes an interface and a processor. The interface is configured to receive from a calibration probe multiple data points acquired in an organ of a patient, each data point including (i) a respective position of the calibration probe, and (ii) a respective set of electrical values indicative of respective impedances between the position and multiple electrodes attached externally to the patient. The processor is configured to construct a mapping between sets of the electrical values and respective positions in the organ, by performing for each received data point: if the mapping already contains one or more existing data points in a predefined vicinity of the data point, the one or more existing data points are adjusted responsively to the received data point, and, if the predefined vicinity does not contain any existing data points, the received data point is added to the mapping.

The present invention will be more fully understood from the following detailed description of the embodiments thereof, taken together with the drawings in which:

BRIEF DESCRIPTION OF THE DRAWINGS

FIG. 2 is a schematic, pictorial illustration of a method for constructing a mapping of an organ, in accordance with an embodiment of the present invention.

DETAILED DESCRIPTION OF EMBODIMENTS

Overview

Figure 1:
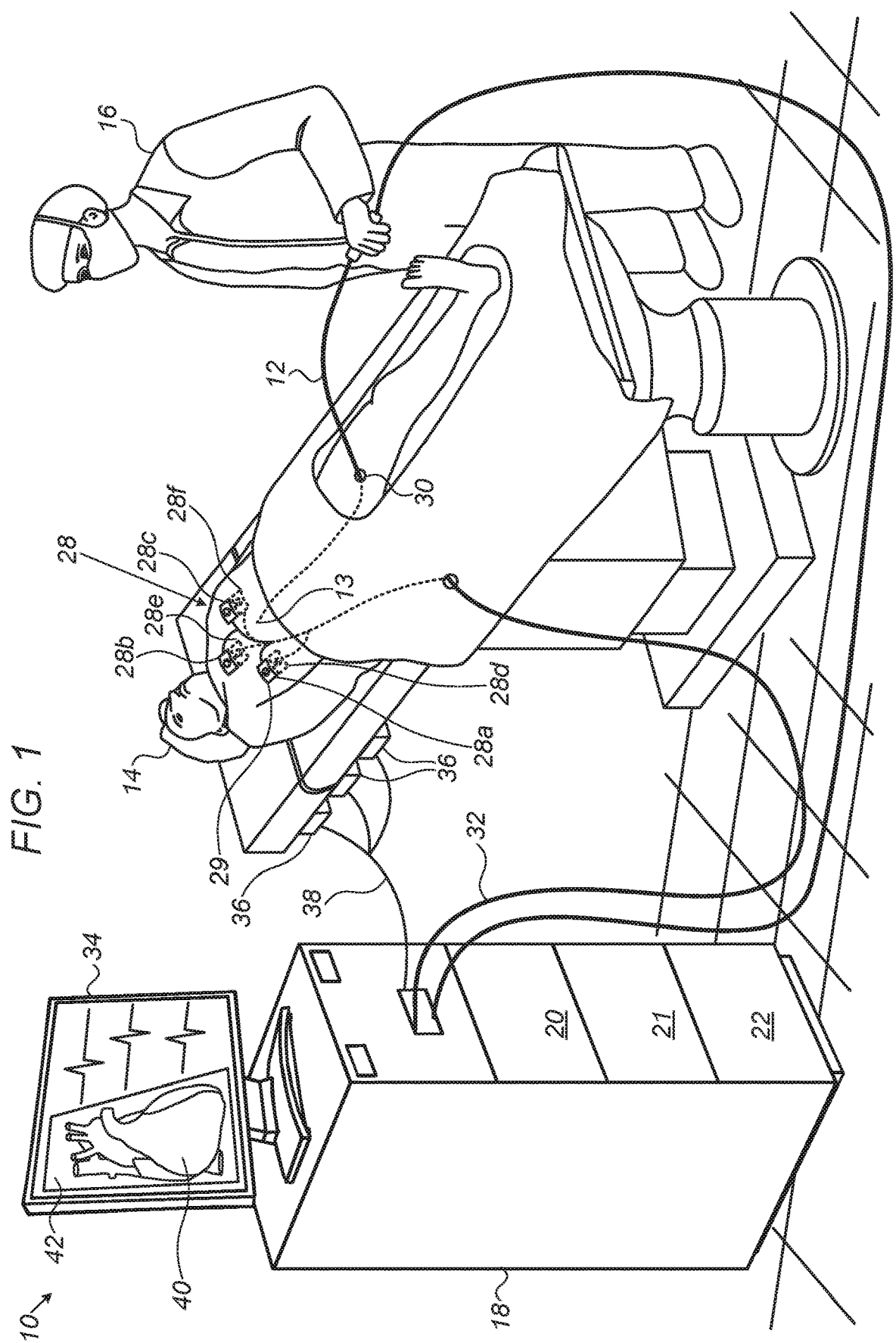
FIG. 1 is a schematic, pictorial illustration of a system for ablating tissue of a patient, in accordance with an embodiment of the present invention.

Embodiments of the present invention that are described herein below provide techniques for improving resolution and efficiency of impedance-based mapping and position tracking.

In some embodiments, a bio-impedance measuring system, such as an active current location (ACL) system, is used in tracking the position of a catheter, or another medical probe, in a patient body. In ACL, tracking the catheter is typically based on measuring impedances between the catheter and external body electrodes. Each measurement is then translated into a respective position of the catheter within the body. The translation is typically based on a suitable mapping, which is constructed beforehand and translates electrical values measured using the electrodes, which electrical values are indicative of respective impedances, into a respective position of the catheter.

In the context of the present disclosure and in the claims, the term "electrical value" refers to impedance, current, voltage or to any other suitable electrical value indicative of the impedance.

The design of the mapping is important for achieving high position tracking performance, such as position accuracy, lateral resolution and minimal latency between the actual position of the catheter and the position reported by the ACL system.

In some embodiments, the mapping is constructed using a calibration probe comprising two sensors: a magnetic position sensor of a magnetic position tracking system, and a bio-impedance sensor of the ACL system. The calibration probe is configured to acquire multiple data points at multiple locations in a patient organ (e.g., heart). Each data point comprises a respective position of the probe measured by the magnetic position sensor, and one or more electrical values indicative of tissue impedance values between the probe within the patient body and one or more respective electrodes attached to the patient skin. The collection of data points is referred to herein as the "mapping."

In principle, it is possible to calibrate the ACL system over a grid of three-dimensional (3D) volume pixels (voxels) that together cover the entire volume of the heart. Some of the voxels may be mapped using the calibration catheter, as explained above. After constructing the mapping in this hypothetical scheme, the physician may perform a medical procedure in which he or she navigates a catheter to an unvisited location in the heart. The ACL system may receive one or more impedance measurements at the unvisited location, and calculate the position of the catheter using the measured impedance, e.g., by interpolating adjacent mapped voxels of the mapped grid. Calculating the position based on interpolation of voxels, however, typically consumes significant computing and memory resources. For example, configuring a small voxel size results in accurate position measurement but causes high latency and complexity, and vice versa.

In some embodiments that are described herein, a processor of the ACL system is configured to construct a mapping between the impedance values and the respective positions in the heart using the acquired data points efficiently, not using a regular grid of voxels. In this embodiment, the processor is configured to check, for each new data point acquired, whether the mapping already contains one or more existing data points in a predefined vicinity of the new data point. If so, the processor adjusts one or more of the existing data points in the mapping responsively to the new data point. If the predefined vicinity does not contain any existing data points, the processor is configured to add the new data point to the mapping.

The disclosed technique enables: (i) improved spatial resolution and positioning accuracy by using one-dimensional data points rather than 3D voxels, and (ii) improved system latency by reducing the amount of computation and memory resources required in tracking the position of the catheter.

System Description

FIG. 1 is a schematic, pictorial illustration of a system 10 for ablating tissue of a patient 14, in accordance with an embodiment of the present invention. In some embodiments, system 10 supports (i) constructing of a mapping prior to the ablation, for mapping a heart 40 of patient 14, and (ii) using the constructed mapping, navigation of a medical tool within heart 40, during an ablation procedure, as will be described in detail below.

In some embodiments, system 10 comprises a catheter 12, comprising a distal tip 13 that comprises a plurality of devices (not shown), such as an ablation electrode, a magnetic position sensor and an impedance sensor. In this configuration, catheter 12 with distal tip 13 is used as a calibration probe, as will be described below. During the mapping phase, (as well as during the ablation procedure), physician 16 may insert catheter 12, via an insertion point 30, into vasculature of patient 14, and may then navigate the catheter tip to the patient's heart. Subsequently, catheter 12 is used for mapping tissue of heart 40 before ablating the tissue.

In some embodiments, an operating console 18 comprises a radiofrequency (RF) generator 22, configured to generate the RF ablation signals applied by catheter 12 on the tissue of heart 40.

In some embodiments, console 18 comprises a processor 20, typically a general-purpose computer, with suitable front end and interface circuits for receiving signals from catheter 12 and for controlling the other components of system 10 described herein. Processor 20 may be programmed in software to carry out the functions that are used by the system, and the processor stores data for the software in a memory (not shown). The software may be downloaded to console 18 in electronic form, over a network, for example, or it may be provided on non-transitory tangible media, such as optical, magnetic or electronic memory media. Alternatively, some or all of the functions of processor 20 may be carried out by dedicated or programmable digital hardware components.

In some embodiments, system 10 further comprises a magnetic position tracking system, and an impedance-based active current location (ACL) system. Each of these systems may be used for tracking the position of distal tip 13 for the purpose of navigating catheter 12 to ablation locations within heart 40 of patient 14.

In some embodiments, the magnetic position tracking system comprises magnetic field-generators 36 placed at known positions external to patient 14 e.g., below the patient's torso. In an embodiment, console 18 assists in carrying out the techniques described herein.

In some embodiments, console 18 comprises a driver circuit 21, configured to drive field-generators 36 via a cable 38. When distal tip 13 is navigated by physician 16 into heart 40, the magnetic position sensor at distal tip 13, generates position signals in response to the sensed external magnetic fields produced by field-generators 36, thereby enabling processor 20 to identify the position of distal tip 13 within the cavity of heart 40.

The magnetic position sensor is connected to interface circuitry coupled to processor 20 at the catheter proximal end. In an embodiment, the position of distal tip 13 is shown on an image 42 of heart 40, which is displayed on a user display 34. In some embodiments, image 42 is acquired using an anatomical imaging system, such as a computerized tomography (CT) system or any other suitable imaging technique.

This method of magnetic-field based position sensing is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

As noted above, system 10 comprises an ACL system, which can serve as an alternative position tracking system to the magnetic-field based system. In some embodiments, the ACL system comprises a plurality of electrodes 28, which are coupled to the body of patient 14, e.g., via patches 29 that adhere to the skin of patient 14. In the example of FIG. 1, system 10 comprises six electrodes, of which electrodes 28a, 28b, and 28c are coupled to the front (e.g., chest) of patient 14, and electrodes 28d, 28e, and 28f are coupled to the back (e.g., torso) of patient 14. As shown in FIG. 1, the electrodes are arranged in pairs as follows: electrodes 28a and 28d are facing one another on the right side of patient 14, electrodes 28c and 28f are facing one another on the left side of patient 14, and electrodes 28b and 28e are facing one another on the upper part of the chest and torso of patient 14.

In other embodiments, system 10 may comprise any suitable number of electrodes, coupled to the patient skin in any suitable arrangement.

Electrodes 28 are typically connected, via a cable 32, to processor 20, which is configured to receive from the electrodes information such as values of impedance, and, based on this information, to estimate the position of distal tip 13 within heart 40 using techniques that will be described below.

Display 34, is typically configured to facilitate performance of the ablation procedure by displaying relevant information to physician 16. For example, processor 20 may register between the coordinate systems of the aforementioned tracking systems and the coordinate system of the CT system (which acquired image 42), so as to display the location and orientation of distal tip 13 within image 42, e.g., by superimposing an icon representing distal tip 13 of catheter 12 over image 42 of heart 40.

As noted above, electrodes 28 are typically used for navigating catheter 12 within the body of patient 14, using impedance-based tracking techniques, such as those described, for example, in U.S. Pat. No. 8,456,182 and US Patent Application Publication 2015/0141798, whose disclosures are incorporated herein by reference. Such techniques involve estimating the location and orientation of distal tip 13 responsively to the different impedances measured between distal tip 13 and each of electrodes 28a-28f. As described above, the estimated location of distal tip 13 may be indicated to the physician as a suitable icon on display 34. Based on this indication, physician 16 may navigate distal tip 13 of catheter 12 to one or more desired locations within heart 40.

In some embodiments, the location and orientation of distal tip 13 at any given time, are typically estimated by applying an electrical signal of a known amplitude to distal tip 13, and the resulting voltages and/or currents are measured at each pair of electrodes 28. In alternative embodiments, the electrical signal may be applied by electrodes 28, and the resulting electrical values are measured by distal tip 13.

In some embodiments, these applied electrical signals cause the pairs of electrodes 28 (e.g., pair of electrodes 28a and 28d, electrodes 28c and 28f, and electrodes 28b and 28e), each of which is located at a different position relative to the catheter, to exhibit different respective electrical values, due to a different amount of electrically-impeding tissue (and therefore, a different degree of impedance) between distal tip 13 and each of the pairs of electrodes 28.

In some embodiments, these measured electrical values are sent, via cable 32, to processor 20, which uses these values to estimate the relative location and orientation of distal tip 13 relative to electrodes 28 (whose positions are known). Alternatively, voltages between the distal tip of the catheter and the electrodes may be generated, and the resulting currents flowing through the electrodes may be measured and used for estimating the location and orientation of distal tip 13.

As described above, physician 16 navigates distal tip 13 to visit at multiple locations within heart 40. In some embodiments, processor 20 is configured to receive from catheter 12 at each of the visited locations, two sets of values. The first set comprises position coordinates from the magnetic position tracking system, and the second set comprises one or more respective electrical values (e.g., a value of current or impedance from each pair of electrodes 28) from the ACL system.

In some embodiments, processor 20 is configured to construct a set of data points that each comprises the position and electrical values measured at a respective position visited by distal tip 13. This set of data points maps multiple selected electrical values into respective positions, and is referred to herein as "mapping." In an embodiment, when completed, the mapping is applied (e.g., during ablation) to electrical values acquired by distal tip 13 and/or electrodes 28, for translating measured electrical values into a position measurement in heart 40. Note that a separate mapping may be constructed for selected respiration operations (for example, after a full inhalation operation, after a full exhalation operation, or a midpoint between inhalation and exhalation operations) of patient 14. In another embodiment, a separate mapping is constructed for each pair of electrodes.

Accurate and Efficient Impedance-Based Position Tracking

FIG. 2 is a schematic, pictorial illustration of a method for constructing a mapping that translates impedance measurements to positions, to be used for accurate position tracking in an ACL system, in accordance with an embodiment of the present invention.

In some embodiments, processor 20 is configured to apply scattered interpolant techniques to perform interpolation on a given 3D data set of scattered data, such as impedance values acquired in heart 40. The scattered interpolant returns one or more interpolant value for the given 3D data set. Further details regarding scattered interpolant techniques are provided by Isaac Amidror, in "Scattered data interpolation methods for electronic imaging systems: a survey," Journal of Electronic Imaging 11(2), 157-176 (April 2002), which is incorporated herein by reference.

In some embodiments, processor 20 is configured to calculate the mapping for data points 52A, 54A and 56 acquired in heart 40 by distal tip 13. In some embodiments, each data point having an index denoted "i" is associated with position coordinates (e.g., $X_i$, $Y_i$, $Z_i$ in Cartesian coordinates) and three values of impedance, referred to herein as Vf1, Vf2, and Vf3. The position coordinates are acquired by the magnetic position tracking system, and the three values refer to respective impedances measured between distal tip 13 and each of the respective pairs of electrodes (electrodes 28a and 28d, electrodes 28c and 28f, and electrodes 28b and 28e) of the ACL system.

In the example of FIG. 2, data points 52A, 54A and 56 are existing (i.e., already collected) data points, and a data point 50 is a data point newly acquired by catheter 12.

In some embodiments, processor 20 checks whether one or more of the existing data points are within a predefined vicinity represented, for example, by a circle 58 having a radius, "R," and centered about a data point 50. In the example of FIG. 2, data points 52A and 54A are within the predefined vicinity and data point 56 is outside the predefined vicinity. Subsequently, processor 20 adjusts the position and impedance values of data points 52A and 54A responsively to the position and impedance values measured for data point 50.

In an embodiment, the adjustment may be carried out by calculating a weighted arithmetic average over data points 50, 52A and 54A, and consequently, replacing data points 52A and 54A with adjusted data points 52B and 54B. Note that the adjusted mapping comprises only data points 52B, 54B and 56, whereas data points 52A, 54A and 50 are removed from the mapping.

In this embodiment, data points 52B and 54B comprise different respective positions and impedance values compared to respective data points 52A and 54A. Note that the location and impedance values of data point 56 are not affected by data point 50, and therefore, remain unchanged.

In alternative embodiments, any other suitable adjustment method may be carried out instead of calculating the weighted arithmetic average over the data points within the predefined vicinity defined by the value of R. Note that setting the value of R depends on several parameters, such as the anatomy of heart 40 (e.g., volume of the heart), the type of ablation procedure, the location within heart 40 and the respective position and values of impedance. In the example of FIG. 2, the radius R has a length on the order of 1-2 mm, but any other suitable value of R may be used.

In alternative embodiments, the predefined vicinity may be represented by any other method, such as by a geometrical shape that takes into consideration the shape of the organ in question.

In another embodiment, a newly acquired data point (not shown) may not have any existing point within the predefined vicinity. For example, physician 16 may navigate distal tip 13 to a region not yet visited within heart 40.

Furthermore, even in an already visited region, such as the region depicted in FIG. 2, the predefined value of R may be less than 0.5 mm so that none of existing data points 52A, 54A and 56 fall within the predefined vicinity around data point 50. In this embodiment, data point 50 will be added as a new entry to the mapping having the position and impedance values as originally acquired by distal tip 13.

Subsequently, physician 16 completes the mapping of regions of interest within heart 40, and processor 20 completes the construction of the respective mapping as described above. The aforementioned techniques enable reducing the amount of data points in the mapping, thereby, enabling fast computation of the position of distal tip 13 by the ACL system, without using the magnetic position tracking system.

During the ablation procedure, physician 16 navigates catheter 12, or another catheter comprising an impedance sensor and an ablation electrode, in heart 40. When physician 16 navigates distal tip 13 to an unvisited location, processor 20 receives from catheter 12 the measured values of impedance, performs a query among the existing data points of the mapping, and calculates the position of distal tip 13 at the unvisited location.

In practice, the number of data points in the mapping may be on the order of several thousands. During the query operation, in some embodiments, processor 20 may sort the data points already contained in the mapping in ascending order of their distance from the new, unvisited location.

This sorting process enables the processor to efficiently identify existing data points (if any) that fall within the predefined vicinity of the unvisited location. The sorting process should be fast, so as to provide physician 16 with a low-latency real-time measurement of the position of distal tip 13 within heart 40.

In an embodiment, processor 20 is configured to conduct a binary search (or any other suitable type of search) based on values of impedance measured in the vicinity of the current position of distal tip 13.

It will be understood that by assuming a physical motion of distal tip 13 within heart 40, the difference in values of impedance among two adjacent locations is expected to be small. When physician 16 navigates distal tip 13 to an unvisited location (also referred to herein as a newly acquired point), processor 20 receives from catheter 12 the measured values of impedance at the unvisited location.

In some embodiments, during the procedure, processor 20 may sort the data points already contained in the mapping in ascending order of their values of impedance relative to the new, unvisited location.

In an embodiment, during the binary search among the existing data points of the mapping, processor 20 is configured to apply a predefined range of values comprising the measured values of impedance at the unvisited location. This technique enables shortening the calculation time of the position of the newly acquired point in heart 40.

For example, in a mapping comprising a number of 10,000 data points, only 1,000 of the data points are expected to have +/−5% of the impedance value measured at the newly acquired point.

In this embodiment, processor 20 is expected to complete the query, and to report the newly acquired position of distal tip 13, in about 10% of the time, on average, compared to a full query carried over the entire set of 10,000 data points.

Figure 3:
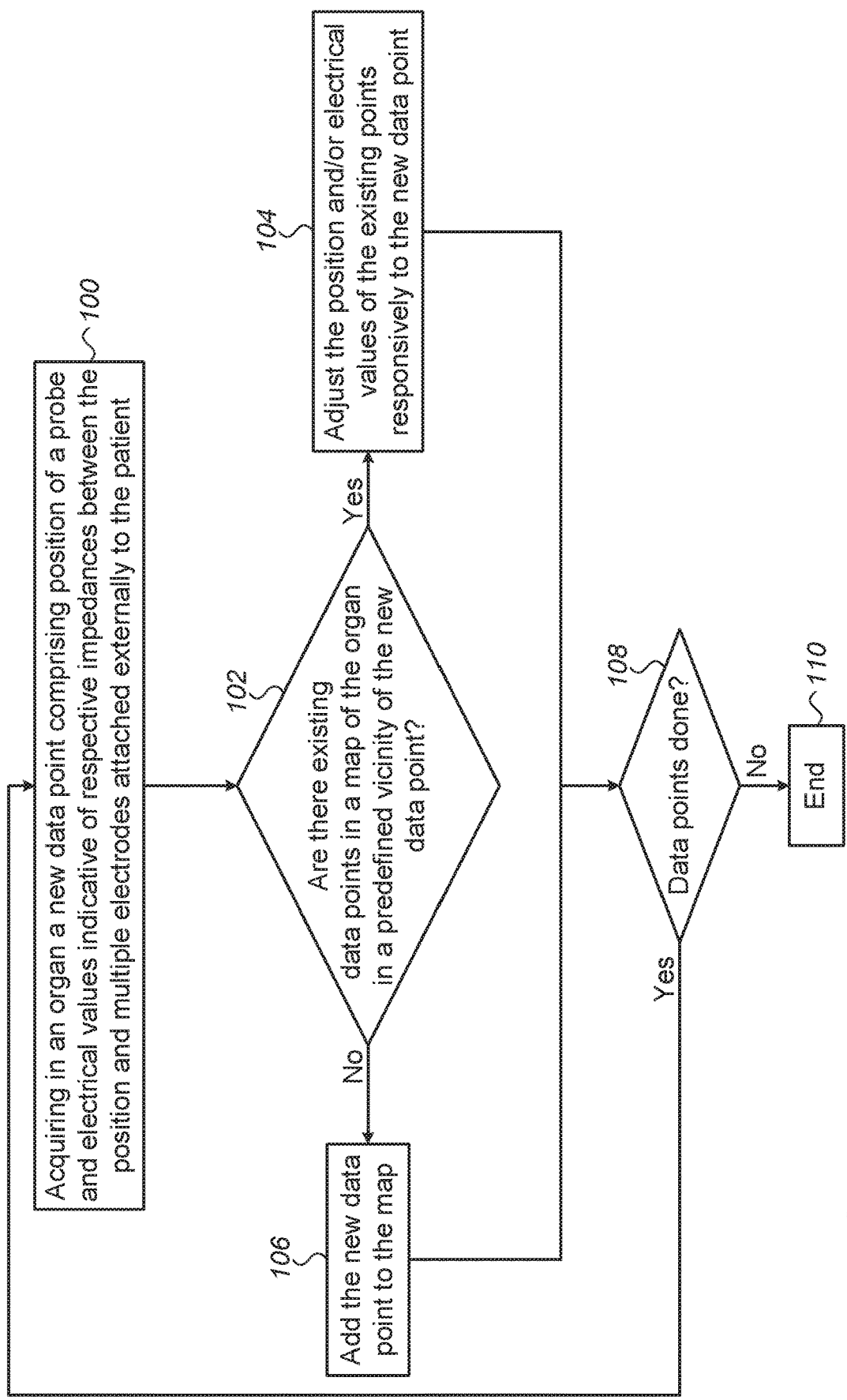
FIG. 3 is a flow chart that schematically illustrates a method for constructing a mapping of an organ, in accordance with an embodiment of the present invention.

FIG. 3 is a flow chart that schematically illustrates a method for constructing a mapping of the ACL system in heart 40, in accordance with an embodiment of the present invention. The method begins at an acquisition step 100, in which physician 16 navigates distal tip 13, which acquires a new data point, such as data point 50, in heart 40. In some embodiments, data point 50 comprises the position of distal tip 13, acquired by the magnetic position sensor, and electrical values indicative of respective impedances between distal tip 13 and the pairs of electrodes 28 (e.g., pair of electrodes 28a and 28d, pair of electrodes 28c and 28f, and pair of electrodes 28b and 28e) attached on the skin of patient 14.

At a first decision step 102, processor 20 checks whether existing data points of the mapping, such as data points 52A, 54A and 56, fall within the predefined vicinity (e.g., as determined by the value of radius R) centered about data point 50.

If the mapping already contains one or more existing data points within the predefined vicinity of data point (e.g., circle 58), the method applies a mapping adjustment step 104, in which processor 20 adjusts the existing data points (e.g., data points 52A and 54A) within circle 58, responsively to data point 50. In this embodiment, processor 20 replaces data points 52A and 54A with respective data points 52B and 54B having the adjusted position and electrical values. Note that the location and impedance values of data point 56 will not be affected by data point 50, and data point 50 will be excluded from the mapping.

In case circle 58 does not contain any existing data point, the method continues to a new data point setting step 106, in which processor 20 registers data point 50 as an existing data point having the position and electrical values as originally acquired by distal tip 13.

At a second decision step 108, if a new data point is acquired by distal tip 13, the method loops back to acquisition step 100. Alternatively, in case distal tip 13 does not send a new data point, the mapping is completed and the method is ended at an ending step 110.

Although the embodiments described herein mainly address mapping a human heart in an ablation procedure, the methods and systems described herein can also be used in mapping of any organ comprising conductive materials, such as a blood pool.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method, comprising:
   receiving from a calibration probe multiple data points acquired in an organ of a patient, each data point comprising (i) a respective position of the calibration probe, and (ii) a respective set of electrical values indicative of respective impedances between the position and multiple electrodes attached externally to the patient;
   constructing an adjusted mapping between sets of the electrical values and respective positions in the organ, by performing for each newly acquired data point:
      if a mapping contains one or more existing data points in a predefined vicinity of each newly acquired data point, replacing, in response to the position and electrical value for each newly acquired data point in the predefined vicinity, the one or more existing data points in the predefined vicinity with adjusted data points having different positions and electrical values than the one or more existing data points in the predefined vicinity, and excluding each of the one or more existing data points in the predefined vicinity and each newly acquired data point,
      if the mapping does not contain any existing data points in the predefined vicinity and contains one or more existing data points outside the predefined vicinity, adding the newly acquired data point with the position and electrical value as acquired by the probe and including each of the one or more existing data points outside the predefined vicinity with an unchanged position and electrical value, and
      if the mapping does not contain any existing data points in the predefined vicinity and does not contain one or more existing data points outside the predefined vicinity, adding the newly acquired data point to the adjusted mapping with the position and electrical value as acquired by the probe; and
   subsequently, tracking a position of a medical probe in the organ using the adjusted mapping.

2. The method according to claim 1, wherein constructing the adjusted mapping comprises finding the one or more existing data points that fall in the predefined vicinity, by sorting at least some of the existing data points in the mapping according to their respective distances from the received data point.

3. The method according to claim 2, wherein sorting the existing data points comprises applying a binary searching technique.

4. The method according to claim 1, wherein the calibration probe comprises a magnetic position sensor of a magnetic position tracking system.

5. The method according to claim 1, wherein the predefined vicinity comprises a circle defined by a radius smaller than 10 mm, centered at the position specified in the received data point.

6. The method according to claim 1, wherein adjusting the one or more existing data points comprises calculating a weighted arithmetic average of the position and the electrical values between the one or more existing data points and the received data point, and adjusting the position and the electrical values of the one or more existing data points by applying a scattered interpolant process.

7. The method according to claim 1, wherein tracking the position comprises:
   receiving from the medical probe, at a given location in the organ, a given set of the electrical values;
   selecting, from among the existing data points of the mapping, data points comprising electrical values falling within a predefined range of electrical values comprising the given set; and
   estimating the position of the medical probe at the given location by identifying one or more of the selected data points having electrical values closest to the electrical values of the given set.

8. The method according to claim 7, wherein identifying the one or more of the selected data points comprises applying a binary searching technique.

9. An apparatus, comprising:
   an interface, configured to receive from a calibration probe multiple data points acquired in an organ of a patient, each data point comprising (i) a respective position of the calibration probe, and (ii) a respective set of electrical values indicative of respective impedances between the position and multiple electrodes attached externally to the patient; and
   a processor, configured to construct an adjusted mapping between sets of the electrical values and respective positions in the organ, by performing for each newly acquired data point:
      if a mapping contains one or more existing data points in a predefined vicinity of each newly acquired data point, replacing, in response to the position and electrical value for each newly acquired data point in the predefined vicinity, the one or more existing data points in the predefined vicinity with adjusted data points having different positions and electrical values than the one or more existing data points in the predefined vicinity, and excluding each of the one or more existing data points in the predefined vicinity and each newly acquired data point, if the mapping does not contain any existing data points in the predefined vicinity and contains one or more existing data points outside the predefined vicinity, adding the newly acquired data point with the position and electrical value as acquired by the probe and including each of the one or more existing data points outside the predefined vicinity with an unchanged position and electrical value, and if the mapping does not contain any existing data points in the predefined vicinity and does not contain one or more existing data points outside the predefined vicinity, adding the newly acquired data point to the adjusted mapping with the position and electrical value as acquired by the probe.

10. The apparatus according to claim 9, wherein the processor is configured to sort at least some of the existing data points in the mapping according to their respective distances from the received data point.

11. The apparatus according to claim 10, wherein the processor is configured to sort the existing data points by applying a binary searching technique.

12. The apparatus according to claim 9, wherein the calibration probe comprises a magnetic position sensor of a magnetic position tracking system.

13. The apparatus according to claim 9, wherein the processor is configured to set the predefined vicinity by applying a circle defined by a radius smaller than 10 mm, centered at the position specified in the received data point.

14. The apparatus according to claim 9, wherein the processor is configured to calculate a weighted arithmetic average of the position and the electrical values between the one or more existing data points and the received data point, and to adjust the position and the electrical values of the one or more existing data points by applying a scattered interpolant process.

15. The apparatus according to claim 9, wherein the processor is configured to receive from the medical probe, at a given location in the organ, a given set of the electrical values; to select, from among the existing data points of the mapping, data points comprising electrical values falling within a predefined range of electrical values comprising the given set; and to estimate the position of the medical probe at the given location by identifying one or more of the selected data points having electrical values closest to the electrical values of the given set.

16. The apparatus according to claim 15, wherein the processor is configured to apply a binary searching technique in identifying the one or more of the selected data points.

* * * * *